(12) United States Patent
Yang et al.

(10) Patent No.: US 8,361,441 B2
(45) Date of Patent: *Jan. 29, 2013

(54) **DETECTION AND THERAPY OF BACTERIAL INFECTION CAUSED BY *ENTEROBACTERIACEAE***

(75) Inventors: Yi-Yuan Yang, Taipei (TW); Hsueh-Hsia Wu, Taipei (TW); Sy-Jye Leu, Taipei (TW); Neng-Yao Shih, Miaoli County (TW); I-Jen Huang, Tainan (TW); Wen-Shyang Hsieh, Taipei (TW); Ko-Jiunn Liu, Miaoli County (TW); Shih-Yi Huang, Taipei (TW); Yung-Luen Shih, Taipei (TW); Chi-Hsin Lee, Taipei (TW); Yuan-Soon Ho, Taipei (TW); Shih-Lan Hsu, Taipei (TW)

(73) Assignee: Taipei Medical University, Taipei (TW)

( * ) Notice: Subject to any disclaimer, the term of this patent is extended or adjusted under 35 U.S.C. 154(b) by 154 days.

This patent is subject to a terminal disclaimer.

(21) Appl. No.: 12/569,363

(22) Filed: Sep. 29, 2009

(65) Prior Publication Data
US 2010/0087373 A1      Apr. 8, 2010

Related U.S. Application Data

(63) Continuation-in-part of application No. 12/046,165, filed on Mar. 11, 2008, now Pat. No. 7,608,247.

(51) Int. Cl.
*A61K 49/00* (2006.01)
*A61K 39/02* (2006.01)
*A61K 39/112* (2006.01)

(52) U.S. Cl. .... 424/9.1; 424/9.2; 424/130.1; 424/150.1; 424/163.1; 424/164.1; 424/184.1; 424/234.1; 424/257.1; 424/258.1; 424/259.1

(58) Field of Classification Search .......... 424/9.1, 424/9.2, 130.1, 150.1, 163.1, 164.1, 184.1, 424/234.1, 257.1, 258.1, 259.1
See application file for complete search history.

(56) References Cited

U.S. PATENT DOCUMENTS 7,608,247 B2 * 10/2009 Yang et al. ............ 424/9.2
7,807,139 B2 * 10/2010 Yang et al. ............ 424/9.2

OTHER PUBLICATIONS

Wertz, J.E., et al. A molecular phylogeny of enteric bacteria and implications for bacterial species concept. J. Evol. Biol., vol. 16, pp. 1236-1248, 2003.*

* cited by examiner

*Primary Examiner* — Rodney P. Swartz
(74) *Attorney, Agent, or Firm* — WPAT, P.C.; Anthony King

(57) ABSTRACT

The present invention provides a method for the treatment and/or prevention of bacterial infection caused by Enterobacteriaceae bacteria in central nervous system and/or peripheral blood circulation in a mammal by administering effective amount of outer membrane protein A (OmpA) or its derivatives to a mammal. Also provided are a method for vaccinating a mammal to produce an antibody against bacterial infection caused by Enterobacteriaceae family in central nervous system and/or peripheral blood circulation and a method of detecting or diagnosing bacterial infections caused by Enterobacteriaceae family in central nervous system and/or peripheral blood circulation in a mammal. An antibody and a kit on the basis of the vaccinating method and detecting/diagnosing method are also provided.

15 Claims, 13 Drawing Sheets
(4 of 13 Drawing Sheet(s) Filed in Color)

DETECTION AND THERAPY OF BACTERIAL INFECTION CAUSED BY ENTEROBACTERIACEAE

CROSS-REFERENCE TO RELATED APPLICATIONS

This application claims priority to, and is a Continuation in part of, U.S. patent application Ser. No. 12/046,165, filed on Mar. 11, 2008, now U.S. Pat. No. 7,608,247, which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

FIELD OF THE INVENTION

The present invention is directed to a method for the treatment and/or prevention and/or diagnosis of bacterial infection caused by Enterobacteriaceae in central nervous system and/or peripheral blood circulation in a mammal by administering an effective amount of outer membrane protein A or its derivatives to a mammal. On the basis of the method, the invention further provides antibodies against bacterial infection and agents and/or kits for diagnosis and/or treatment of bacterial infection.

BACKGROUND OF THE INVENTION

In general, the central nervous system (CNS) is well defended against infection. The spine and brain are sheathed in tough, protective membranes. The outermost membrane, the dura mater, and the next layer, the arachnoid, entirely encase the brain and spinal cord. However, these defenses are not absolute. In some cases, bacteria gain access to areas within the CNS. Bacterial infections can be pyogenic infections (e.g., meningitis; brain abscess; subdural and epidural abscesses), tuberculosis, neurosyphilis, or leprosy. Typically, bacterial invasion results from the spread of a nearby infection; for example, a chronic sinus or middle ear infection can extend beyond its initial site. Bacteria may also be conveyed to the CNS from distant sites of infection by the bloodstream. In rare cases, head trauma or surgical procedures may introduce bacteria directly into the CNS. However, the source of infection cannot always be identified.

The goal of treatment of a bacterial infection is to stop the infection, relieve symptoms, prevent complications, and, if necessary, provide life support. A two-pronged approach is taken to treat bacterial infections. First, antibiotic therapy against an array of potential infectious bacteria is begun. The second stage involves surgery to drain the infected site. Once the bacterial species is identified, drug therapy can be altered to a more specific antibiotic. However, surgery may not be an option in some cases, such as when there are numerous sites of infection or when infection is located in an inaccessible area of the brain.

Outer membrane protein A (OmpA) was initially described by Henning and coworkers in 1975. It has 325 amino acid residues and exhibits heat-modifiable electrophoretic mobility on SDS-PAGE. The N-terminal domain of OmpA is comprised of 177 amino acids and is believed to traverse the outer membrane eight times. OmpA is involved in maintaining the shape of bacteria, serves as a phage receptor and a receptor for F-mediated conjugation, and has limited pore-forming properties. OmpA enhances uptake of LPS into macrophages and has been reported to be involved in $E.$ $coli$ invasion of the central nervous system. WO 9201001 provides a method for producing pure cloned outer membrane proteins, and to provide a method for their renaturation so as to regain biologically or immunologically active epitopes which are capable of eliciting the production of antibodies in animals. Pascale Jeannin et al. reports that outer membrane protein A (OmpA) is a class of protein highly conserved among the Enterobacteriaceae family throughout evolution and OmpA appears as a new type of pathogen-associated molecular pattern (PAMP) usable as a vector in anti-infectious and therapeutic antitumor vaccines to elicit CTLs (Vaccine, Volume 20, Supplement 4, 19 Dec. 2002, pages A23-A27).

However, there are no reports relating to the new use of an outer membrane protein A and its derivatives in the treatment and/or prevention and/or diagnosis of bacterial infection in central nervous system and/or peripheral blood circulation.

SUMMARY OF THE INVENTION

An object of the invention is to provide a method for the treatment and/or prevention of bacterial infection caused by Enterobacteriaceae family in central nervous system and/or peripheral blood circulation in a mammal, which comprises administering to said mammal an effective amount of an outer membrane protein A (OmpA) from Enterobacteriaceae family Another object of the invention is to provide a method for vaccinating a mammal to produce an antibody against bacterial infection caused by Enterobacteriaceae family in central nervous system and/or peripheral blood circulation, which comprises administering to said mammal an effective amount of an OmpA from Enterobacteriaceae family.

Another object of the invention is to provide an isolated antibody obtained from the vaccinating method of the invention and a therapeutic or diagnostic agent containing the antibody of the invention.

A further object of the invention is to provide a method of detecting or diagnosing bacterial infections caused by Enterobacteriaceae family in central nervous system and/or peripheral blood circulation in a mammal, which comprises coating a first specific anti-OmpA antibody onto a matrix surface that can immunospecifically bind to OmpA molecule in blood or OmpA on bacterial membrane, adding a sample from peripheral blood circulation and/or the central nervous system to the matrix, adding a second anti-OmpA antibody with a label, and detecting the binding of the anti-OmpA antibodies to the OmpA molecule or OmpA on bacterial membrane, wherein the binding result indicates that the mammal may suffer from the bacterial infections in the peripheral blood circulation and/or the central nervous system, and wherein the OmpA is from Enterobacteriaceae family.

Another further object of the invention is to provide a kit for diagnosis of bacterial infection caused by Enterobacteriaceae bacteria in the central nervous system and/or peripheral blood circulation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
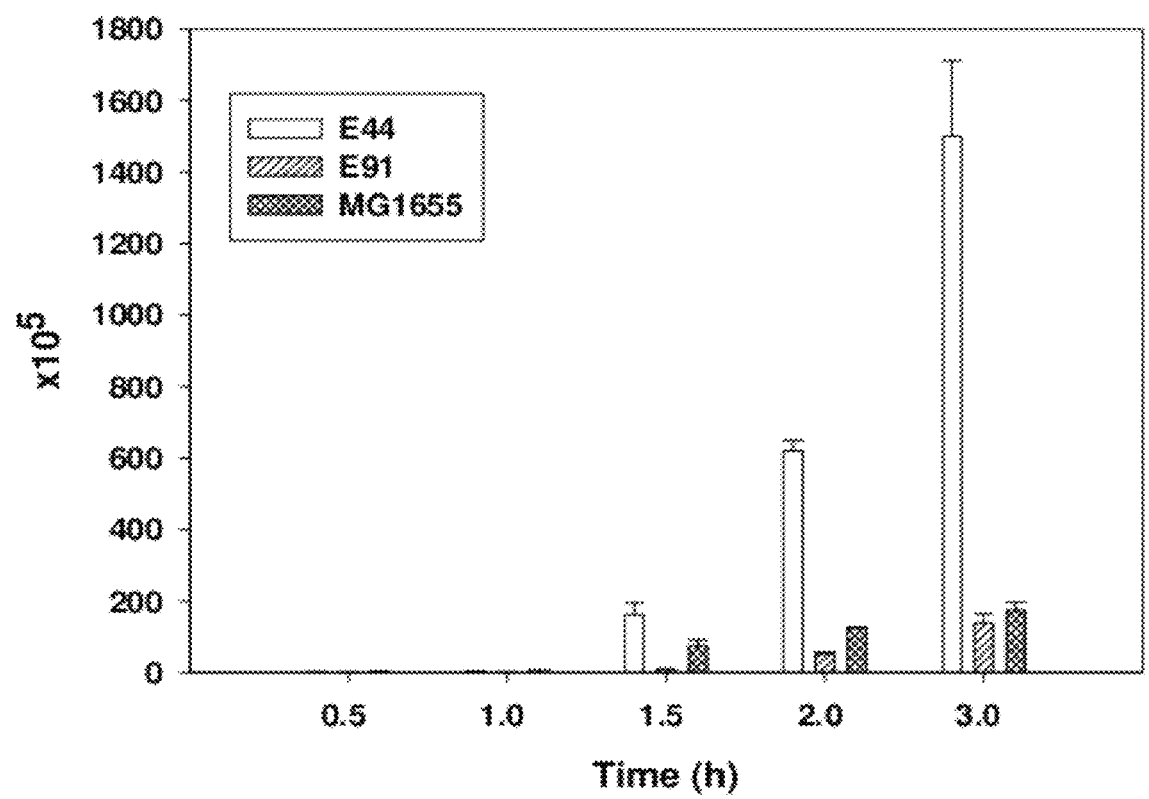
FIG. 1 shows the time course of $E.$ $coli$ strain adhesion.

The invention unexpectedly found that the outer membrane protein A (OmpA) can be used to treat and/or prevent and/or diagnose bacterial infection in central nervous system and/or peripheral blood circulation. In addition, an antibody binding to OmpA has been developed to assay OmpA levels in a biological sample and to detect or diagnose bacterial infection in central nervous system and/or peripheral blood circulation. Such an antibody also can be used to rapidly detect whether a bacterial infection (such as sepsis) is caused by Enterobacteriaceae bacteria so that a doctor can quickly and correctly select antibiotics for treatment to reduce mortality and improve prognosis.

The invention provides a method for the treatment and/or prevention of bacterial infection in central nervous system and/or peripheral blood circulation in a mammal, which comprises administering to said mammal an effective amount of an outer membrane protein A or its derivatives.

The "central nervous system" used herein denotes to that part of the nervous system that consists of the brain and spinal cord. The "peripheral blood circulation" denotes to the blood in the systemic circulation.

The "bacterial infection" used herein denotes the infection caused by Gram-negative bacteria. Preferably, the bacterial infection is caused by Enterobacteriaceae or other Gram-negative bacteria. More preferably, the bacterial infection is caused by *Shigella*, *Salmonella*, *Klebsiella*, *Escherichia*, *Citrobacter*, *Enterobacter* or *Serratia*. Most preferably, the bacterial infection is caused by *Escherichia coli*, *Klebsiella pneumoniae*, *Salmonella typhi*, *Enterobacter aerogenes*.

The "outer membrane protein A (OmpA)" used herein denotes to any OmpA from Gram-negative bacteria and any recombinant OmpA. OmpA is an abundant structural protein of the outer membrane of Gram-negative bacteria. The "OmpA derivatives" denotes to proteins derived from OmpA, which have same function as that of OmpA. For example, OmpA recombinants having same function with OmpA are OmpA derivatives. Preferably, OmpA or its derivative is obtained from Enterobacteriaceae or other Gram-negative bacteria. OmpA is a class of protein highly conserved among the Enterobacteriaceae family (see Vaccine, Volume 20, Supplement 4, 19 Dec. 2002, pages A23-A27), so persons skilled in the art recognize that OmpA from various bacteria may have the same function. Nguyen T N et al. finds that after alignment, the amino acid sequences of OmpAs of *Escherichia coli*, *Klebsiella pneumoniae*, *Salmonella typhi*, *Enterobacter aerogenes* have high similarity (Gene 1998 210:93).

In one embodiment, OmpA or its derivative is obtained from Enterobacteriaceae bacteria. Preferably, the Enterobacteriaceae bacteria are selected from the group consisting of *Escherichia*, *Shigella*, *Salmonella*, *Citrobacter*, *Klebsiella*, *Serratia* and *Enterobacter*. More preferably, the Enterobacteriaceae bacteria are selected from the group consisting of *Escherichia coli*, *Shigella sonnei*, *Shigella flexneri*, *Salmonella typhi*, *Salmonella* group A, *Salmonella* group B, *Salmonella* group D, *Citrobacter freundii*, *Citrobacter koseri*, *Klebsiella pneumoniae*, *Klebsiella oxytoca*, *Enterobacter aerogenes*, *Enterobacter cloacae*, *Serratia marcescens*. Further more preferably, the Enterobacteriaceae bacteria is *Escherichia coli*, *Klebsiella pneumoniae*, *Salmonellatyphi*, or *Enterobacter aerogenes*. Most preferably, the Enterobacteriaceae bacteria is *Escherichia coli* or *Klebsiella pneumoniae*.

According to one embodiment of the invention, a recombinant *E. coli* OmpA can effectively treat an infection caused by *Escherichia coli*, *Klebsiella pneumoniae*, *Salmonella typhi*, or *Enterobacter aerogenes*.

According to the invention, a therapeutically effective amount of OmpA or its derivatives of the invention can be administered to a mammal, including a human or non-human mammal, suffering from bacterial infection in both central nervous system and/or peripheral blood system. According to the invention, the administration of OmpA or its derivatives of the invention can be carried out in various ordinary ways. Administration forms suitable for oral administration are those which function according to the state of the art and deliver OmpA or its derivatives of the invention in a rapid and/or modified way, for example, tablets (uncoated or coated tablets, for example with coatings which are resistant to gastric juice or dissolve slowly or are insoluble and which control the release of the compound of the invention), tablets which rapidly disintegrate in the mouth, or films/wafers, films/lyophilisates, capsules (for example hard or soft gelatin capsules), sugar-coated tablets, granules, pellets, powders, emulsions, suspensions, aerosols or solutions.

Parenteral administration includes intravenous drip or infusion, subcutaneous, intraperitoneal or intramuscular injection, pulmonary administration, e.g., by inhalation or insufflation, or intrathecal or intraventricular administration. Administration forms suitable for parenteral administration are, inter alia, injection and infusion preparations in the form of solutions, suspensions, emulsions, lyophilisates or sterile powders.

Oral or parenteral administration is preferred, especially oral and intravenous administration. Intravenous dosage is particularly preferred for example for the treatment of acute central nervous system infection.

OmpA or its derivatives used according to the invention can be converted into suitable pharmaceutical compositions. This can take place in a known manner by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking tastes and/or odors.

The administration form of the invention comprises 0.0001% to 10% by weight of OmpA or its derivatives, preferably 0.5% to 5% by weight of OmpA or its derivatives. The time of treatment with the pharmaceutical composition of the invention is determined on the basis of severity of the disease to be treated and the conditions of individual patients. A doctor shall determine the adequate amount of time of treatment with the pharmaceutical composition of the invention.

The invention also provides a method for vaccinating a mammal to produce an antibody against bacterial infection in central nervous system and/or peripheral blood circulation, which comprises administering to said mammal an effective amount of an outer membrane protein A or its derivatives. In view of the discovery that OmpA can treat and/or prevent and/or diagnose bacterial infection in central nervous system and/or peripheral blood circulation, OmpA was introduced to an animal for vaccination. It is found that OmpA can induce specific antibody production.

The invention also provides an isolated antibody obtained from the above method which specifically binds to OmpA. In one embodiment, the antibody is a monoclonal antibody, polyclonal antibody or a synthetic antibody or an antibody fragment thereof. Preferably, the antibody is an anti-OmpA IgY antibody. More preferably, the antibody is a mammal or avian anti-OmpA IgY antibody. More preferably, the anti-OmpA IgY antibody is from pig, rabbit, mouse, monkey, horse, goat, cow, sheep, chicken or duck. Most preferably, the antibody is a chicken or duck anti-OmpA IgY antibody. In another embodiment, the antibody of the invention can treat and/or prevent and/or detect (diagnose) a bacterial infection caused by Enterobacteriaceae bacteria in the central nervous system and/or peripheral blood circulation. Preferably, the Enterobacteriaceae bacteria are selected from the group consisting of *Escherichia*, *Shigella*, *Salmonella*, *Citrobacter*, *Klebsiella*, *Serratia* and *Enterobacter*. More preferably, the Enterobacteriaceae bacteria are selected from the group consisting of *Escherichia coli*, *Shigella sonnei*, *Shigella flexneri*, *Salmonella typhi*, *Salmonella* group A, *Salmonella* group B, *Salmonella* group D, *Citrobacter freundii*, *Citrobacter koseri*, *Klebsiella pneumoniae*, *Klebsiella oxytoca*, *Enterobacter aerogenes*, *Enterobacter cloacae*, *Serratia marcescens*. Further more preferably, the Enterobacteriaceae bacteria is *Escherichia coli*, *Klebsiella pneumoniae*, *Salmonella typhi*, or *Enterobacter aerogenes*. Most preferably, the Enterobacteriaceae bacteria is *Escherichia coli* or *Klebsiella pneumoniae*.

The invention also provides a therapeutic agent, comprising the antibody of the invention.

The antibodies of the invention can be produced by any method known in the art. Polyclonal antibodies to OmpA can be produced by various procedures well known in the art. For example, OmpA can be administered to various host animals including, but not limited to, chicken, rabbits, mice, rats, etc. to induce the production of sera containing polyclonal antibodies specific for OmpA. Preferably, the polyclonal antibody is an anti-OmpA IgY antibody. More preferably, the antibody is a mammal or avian anti-OmpA IgY antibody. More preferably, the anti-OmpA IgY antibody is from pig, rabbit, mouse, monkey, horse, goat, cow, sheep, chicken or duck. Most preferably, the antibody is a chicken or duck anti-OmpA IgY antibody. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Antibodies of the invention can be used to assay the presence of OmpA or OmpA levels in a biological sample using classical serological and immunohistological methods as described herein or as known to those of skill in the art. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as glucose oxidase; radioisotopes, such as iodine ($^{125}$I, $^{121}$I) carbon ($^{14}$C), sulfur ($^{35}$S), tritium ($^{3}$H), indium ($^{121}$In) and technetium ($^{99}$Tc); luminescent labels, such as luminol; and fluorescent labels, such as fluorescein and rhodamine, and biotin.

The antibodies and therapeutic agent of the invention may be administered in any convenient or desired manner, for example by oral or parenteral administration. Conveniently, the pharmaceutical compositions may be administered parenterally, i.e., subcutaneously, intramuscularly or intravenously. For such administration the carrier is preferably an aqueous carrier. A variety of aqueous carriers can be used, e.g. water, buffered water, 0.4% saline, 0.3% glycine and the like. These solutions are sterile and generally free of particulate matter. These agents may be sterilized by conventional, well known sterilization techniques. The agents may contain pharmaceutically acceptable auxiliary substances as required to approximate physiological conditions such as pH adjusting and buffering agents, tonicity adjusting agents and the like, for example sodium acetate, sodium chloride, potassium chloride, calcium chloride, sodium lactate, etc. The concentration of antibody in these formulations can vary widely, i.e. from less than 0.5%, usually 1% to as much as 15 or 20% by weight and will be selected primarily based on fluid volume, viscosity, etc., preferably for the particular mode of administration selected.

The invention also provides a diagnostic agent, comprising the antibody of the invention. The diagnostic or therapeutic agent of the invention can diagnose or treat a bacterial infection caused by Enterobacteriaceae bacteria in the central nervous system and/or peripheral blood circulation.

The invention also provides a kit for diagnosis of bacterial infection caused by Enterobacteriaceae bacteria in the central nervous system and/or peripheral blood circulation, comprising: antibodies of the invention, reagents required for the constitution of the medium favorable for performing the OmpA-antibody reaction, and reagents allowing detection of the formed complex.

The invention further provides a method of detecting or diagnosing bacterial infection in central nervous system and/or peripheral blood circulation in a mammal. In one embodiment, the detection or diagnosis comprises: coating a first specific anti-OmpA antibody onto a matrix surface (such as ELISA plates or magnetic nano-particles) that can immunospecifically bind to OmpA molecules in blood or OmpA on bacterial membranes, adding a sample from peripheral blood circulation and/or the central nervous system to the matrix, adding a second anti-OmpA antibody with a label, and detecting the binding of the anti-OmpA antibodies to the OmpA molecules or OmpA on bacterial membranes, wherein the binding result indicates that the mammal may suffer from the bacterial infections in the peripheral blood circulation and/or the central nervous system.

According to the invention, the first specific anti-OmpA antibody is coated onto the matrix surface using a method and commercial coating buffer known in the art and any appropriate matrix can be used in the method. The matrix is preferably ELISA plates or magnetic nano-particles. The anti-OmpA antibody can specifically bind to OmpA molecules in blood or OmpA on bacterial membranes. To allow the binding detectable, the anti-OmpA antibody specifically binding to OmpA molecules can be detected by using a second anti-OmpA antibody with a label. According to the invention, the term "label" refers to a molecule or moiety having a property or characteristic which is capable of detection. A label may be directly detectable, as with radioisotopes, fluorophores or chemilumiphores; or a label may be indirectly detectable, as with haptens or polynucleotide tails. When indirect labels are used for detection or signaling purposes, they are used in conjunction with a signaling entity complex. A "signaling entity" is a molecule or moiety which provides the detectable property or characteristic. The signaling entity may be direct, as with a colloidal particle (e.g. colloidal gold or selenium); or it may be indirect, as with an enzyme (e.g. alkaline phosphatase, beta.-galactosidase or horseradish peroxidase). Indirect signaling entities may require additional components, e.g. substrate, as is well known in the arm. The "signaling entity complex" includes a signaling entity conjugated to specific binding partner, such as an antibody or polynucleotide. Such conjugates may be prepared according to any known method of conjugation.

According to the invention, kits of the invention preferably include reagents for practicing the methods of the invention, containers for carrying out reactions, substrates for spotting the reaction products, instructions for use, and packaging. Reagents may include wash buffers, reaction mixtures, enzymes, and labels. The kit optionally may comprise a subset of the above-listed components, but preferably includes the antibodies of the invention. The kit also comprises reagents required for the constitution of the medium favorable for performing the OmpA-antibody reaction, and reagents allowing detection of the formed complex.

According to the invention, the binding of the anti-OmpA antibody to the OmpA molecule in peripheral blood or central nervous system can be used to detect the existence of the OmpA molecule. If the OmpA molecule exists in the peripheral blood or central nervous system of a subject, it represents that the subject may be infected by a bacteria with OmpA molecule such as Enterobacteriaceae bacteria. A bacterial infection caused by Enterobacteriaceae bacteria can be quickly and correctly detected, even within one day. Therefore, a doctor can quickly select antibiotics in the treatment of bacterial infection caused by Enterobacteriaceae bacteria (such as sepsis) to reduce mortality and improve prognosis.

EXAMPLE

The following examples illustrate the invention. The invention is not restricted to the examples.

Example 1

Adhesion and Invasion Assay

For total C6 glioma cell-associated bacteria studies, confluent cell monolayers were incubated with respective bacteria strain *E. coli* E44, E91 and MG1655 at indicated time intervals at 37° C. *E. coli* E44 is a K1 strain RE218 (O18:K1: H7) and derived from a cerebrospinal fluid of a neonate with meningitis. *E. coli* E91 is a mutant lacking the entire OmpA gene and generated from strain E44. *E. coli* MG1655 is a nonpathogenic strain and non-invasive in blood brain barrier, so it was used as a control.

In the adhesion assay, the C6 glioma cells were infected with the above-mentioned bacteria strains (MOI (bacteria-to-cell ratio)=10) at indicated time intervals. The C6 glioma cell monolayers were then washed with culture medium three times and lysed in 0.5% Triton X-100. The released bacteria were enumerated by plating on sheep blood agar plates. As shown in the results of the adhesion assay (FIG. 1), the numbers of *E. coli* E44 largely increases over time. However, the numbers of *E. coli* E91 and MG1655 are smaller than *E. coli* E44.

Figure 2:
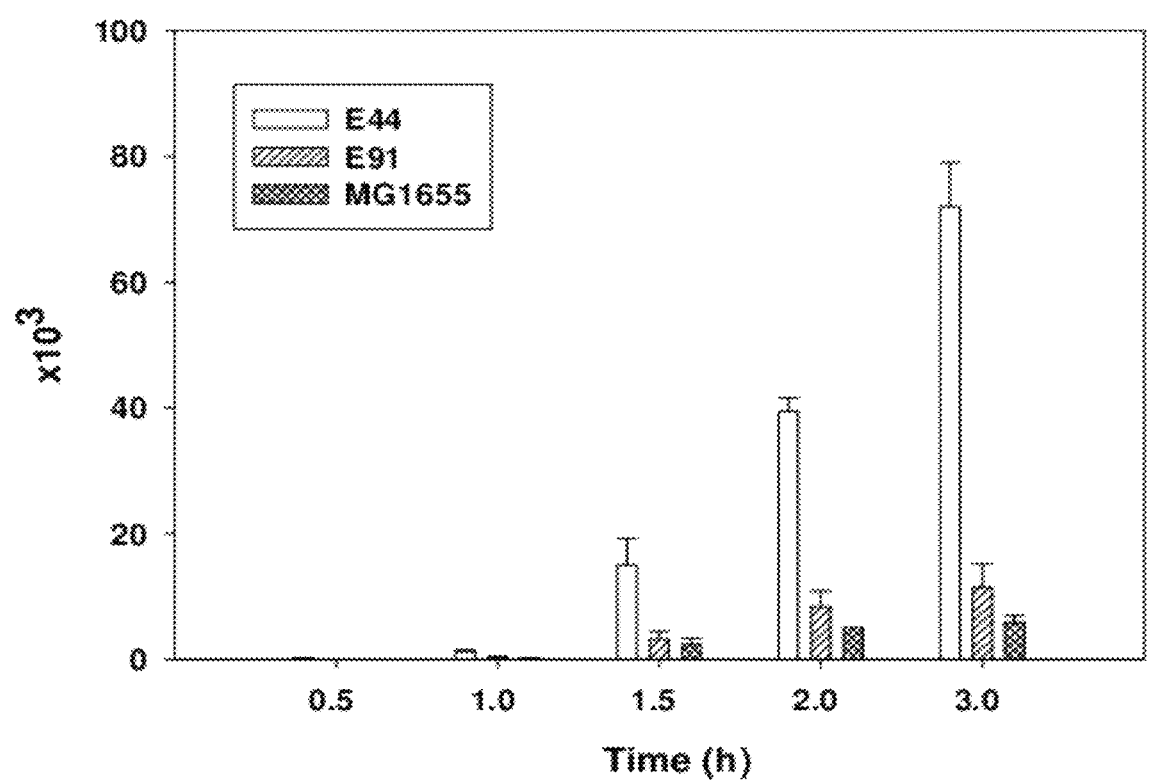
FIG. 2 shows the time course of *E. coli* strain invasion.
Figure 3:
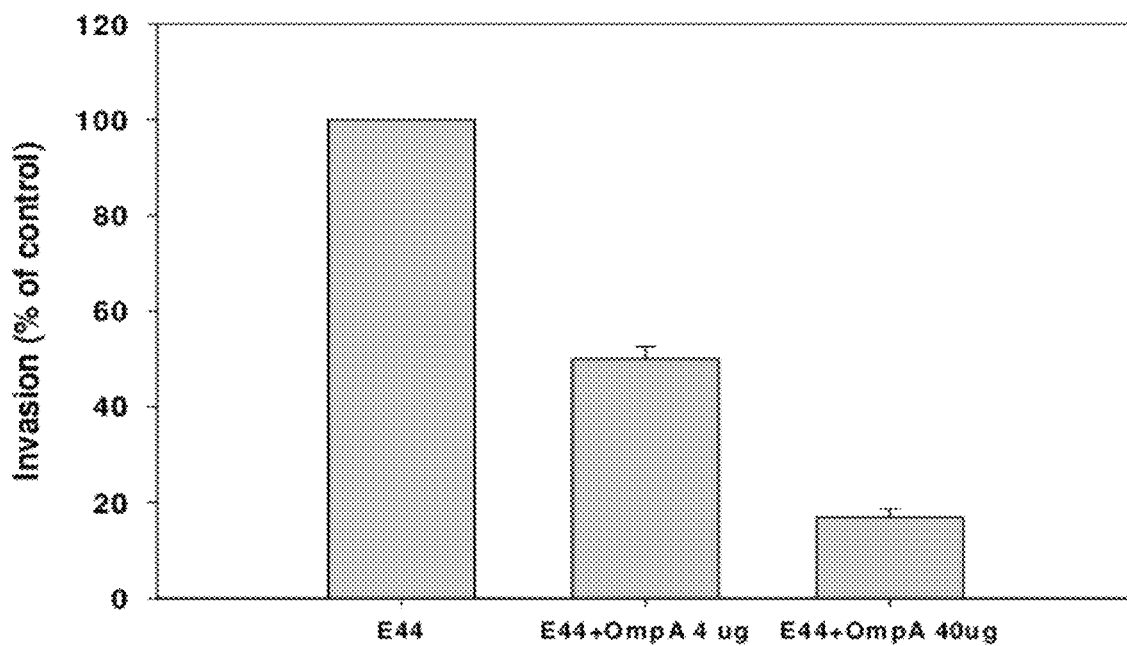
FIG. 3 shows the inhibition of *E. coli* E 44 invasion into C6 glioma cells by OmpA.

In the invasion assay (gentamicin protection assay), for intracellular bacteria studies, the glioma C6 confluent cell monolayers were incubated with the above-mentioned bacteria strain (MOI=10) at indicated time intervals at 37° C. The monolayers were then washed with culture medium three times and further incubated with culture medium containing gentamicin (100 µg ml$^{-1}$) for 2 hours to kill extracellular bacteria. The monolayers were washed three times again and lysed in 0.5% Triton X-100. The released bacteria were enumerated by plating on sheep blood agar plates. As shown in FIG. 2 for the invasion assay, the numbers of *E. coli* E44 are much larger than those of *E. coli* E91 and MG1655. In the invasion inhibition assay, the glioma C6 confluent cell monolayers were infected with *E. coli* E44 (MOI=10) with 4 µg or 40 µg OmpA for 2 hours. The monolayers were then washed with culture medium three times and further incubated with culture medium containing gentamicin (100 µg ml$^{-1}$) for 2 hours to kill extracellular bacteria. The released bacteria were enumerated by plating on sheep blood agar plates. As shown in FIG. 3, the mixtures of *E. coli* E44 and OmpA indeed inhibit the invasion of *E. coli* E44. OmpA can inhibit more than 55% (4 µg) and 80% (40 µg) invasion of *E. coli* E44.

Example 2

Animal Experiments

C57BL/6 mice were obtained from the National Laboratory Animal Center of Taiwan, and kept under pathogen-free conditions. Animal procedures were performed in accordance with the institutional protocol of Taipei Medical University under an approved protocol.

Figure 4:
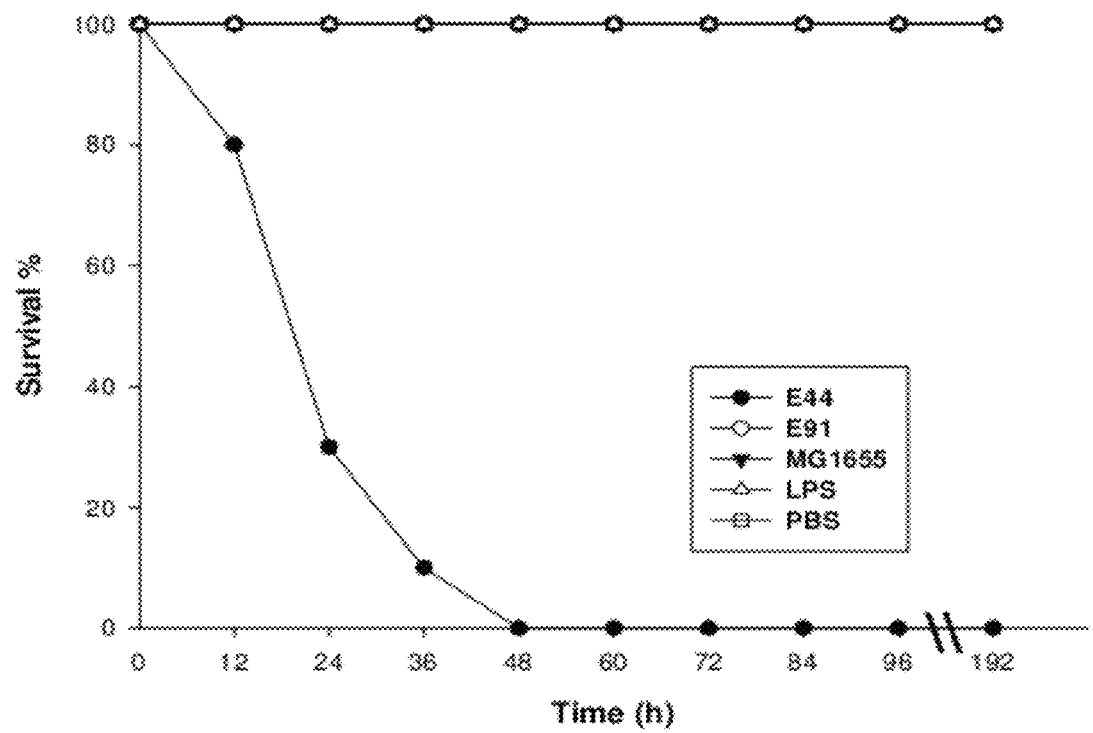
FIG. 4 shows the survival of C57BL/6 mice intracerebrally injected with *E. coli* strains.

8-12 week-old C57BL/6 mice were randomly divided in groups. Each group contained 5 to 10 mice. Mice were anesthetized with pentobarbital sodium salt (50 mg kg$^{-1}$) by intraperitoneal injection, and then each mouse was infected with $5 \times 10^5$ E. coli strains (E44, E91, or MG1655 in 20 µl PBS, or 5 µg LPS in 20 µl PBS by intracerebral injection. 20 µl PBS was used as a control treatment. Survival in C57BL/6 mice after E. coli strains infection was assessed 8 days postadministration. As shown in FIG. 4, all of the mice infected with E. coli E44 died after 2 days.

Figure 5:
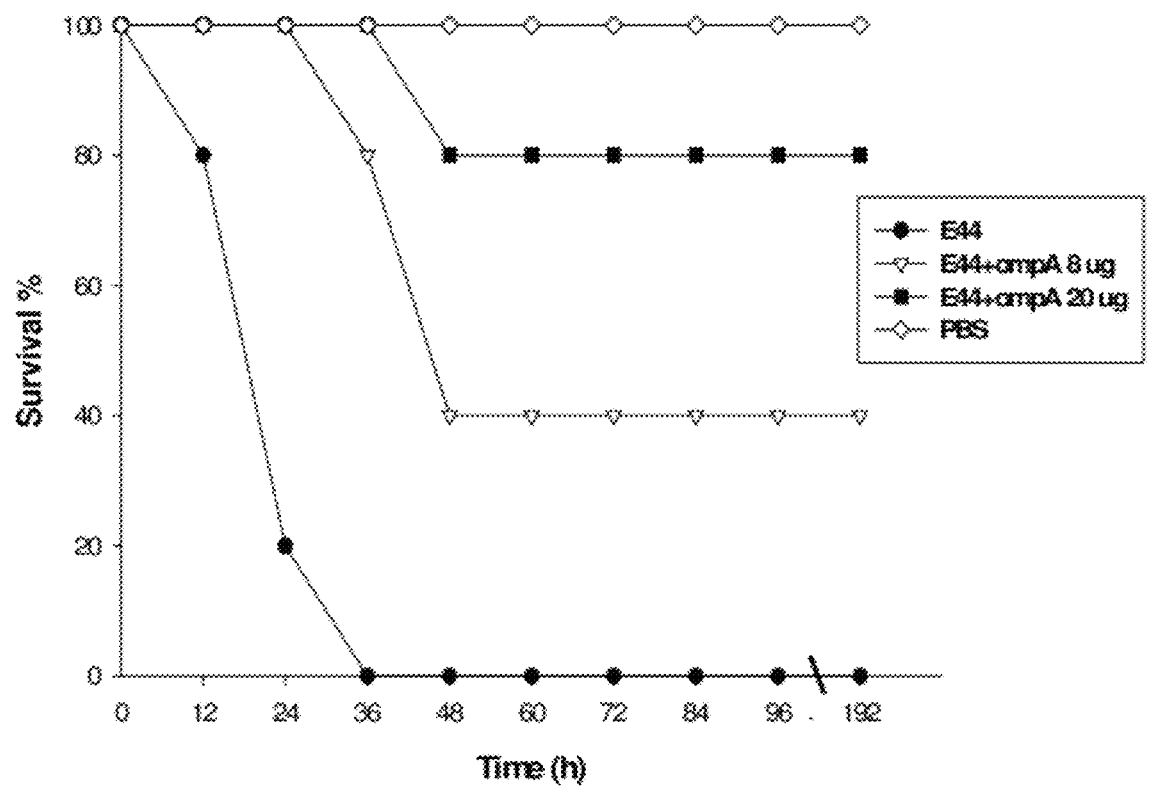
FIG. 5 shows that OmpA prolongs the survival of the mice intracerebrally injected with *E. coli* E44.

To investigate the role of recombinant OmpA in the survival of C57BL/6 mice following intracerebral E44 administration, 8-12 weeks-old C57BL/6 mice were anesthetized with pentobarbital sodium salt (50 mg kg$^{-1}$) by intraperitoneal injection. Then each mouse was infected with E44 $5 \times 10^5$ in 20 µl PBS, without or with premixed with 8 µg or 20 µg recombinant E. coli OmpA, by intracerebral injection. PBS 30 µl was used as a control treatment. Survival in C57BL/6 mice was assessed 8 days postadministration. FIG. 5 shows that OmpA prolongs the survival of the mice intracerebrally injected with E. coli E44. Around 40% and 80% of the mice survived in E. coli E44 with 8 µg OmpA and E. coli E44 with 20 µg OmpA.

Figure 6:
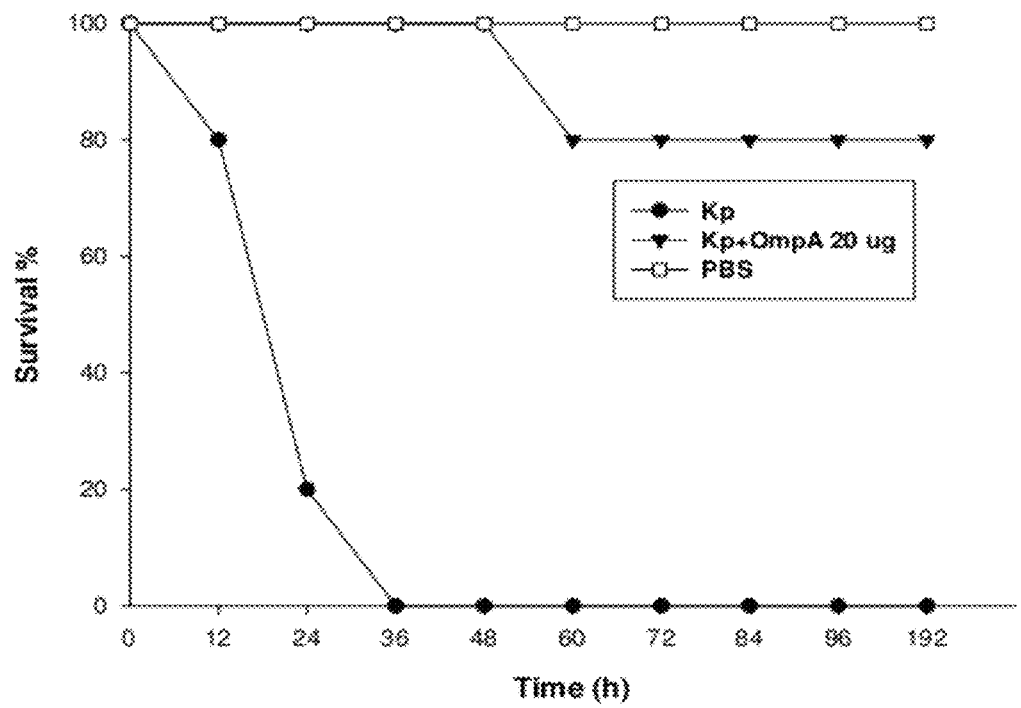
FIG. 6 shows that OmpA prolongs the survival of the mice intracerebrally injected with *Klebsiella pneumoniae*.
Figure 7:
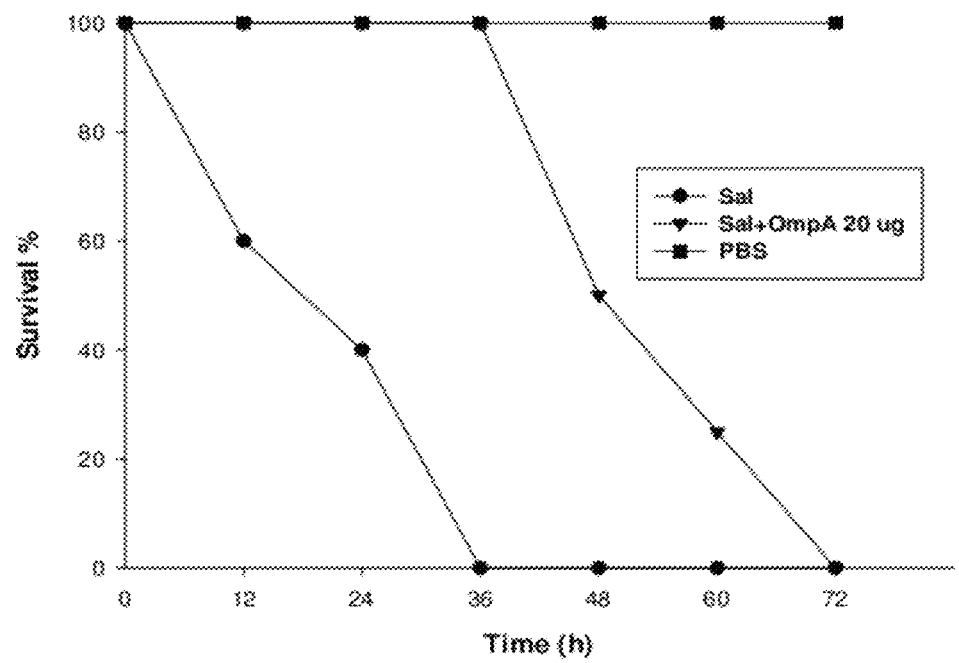
FIG. 7 shows that OmpA prolongs the survival of the mice intracerebrally injected with *Salmonella typhi*.

The above-mentioned mice experiments were performed for the infection caused by Klebsiella pneumoniae or Salmonella typhi and the experimental conditions and steps used were the same as those for E. coli except that only 20 µg recombinant E. coli OmpA was used. FIGS. 6 and 7 show that OmpA prolonged the survival of C57BL/6 mice infected with K. pneumoniae and S. typhi. Around 80% of the mice survived when K. pneumoniae was treated with 20 µg E. coli OmpA. Similarly, when S. typhi was treated with 20 µg E. coli OmpA, the survival of mice was significantly prolonged.

Example 3

Preparation of Chicken Anti-Ompa Antibody of the Invention and its Binding Assay Cloning of OmpA Gene Fragments To amplify the various ompA gene fragments, the primers were designed according to the published nucleotide sequences of E. coli genome (Johns Hopkins University, USA). A polymerase chain reaction (PCR) program consisted of 95° C. for 5 min, 30 cycles of 94° C. for 30 sec, 58° C. for 30 sec, 72° C. for 90 sec, followed by 72° C. for 10 min. The amplified fragments were purified and ligated to pET-21 expression vector after they were treated with Sac I and Xho I (Bio-Labs, USA) respectively. The recombinant plasmid DNAs were transformed into competent E. coli BL-21 by heat shock. Selection was performed with selective LB agar containing ampicillin (50 µg/ml). Subsequently, the plasmid DNAs of several randomly selected clones were isolated, treated with Xho I and Sac I and analyzed by electrophoresis for gene insertion.

Expression and Purification of His-fused OmpA Proteins

The overnight bacterial culture was diluted 100-fold in the LB medium and grown for 1.5 to 2 hr at 37° C. until $OD_{600}$ reached 0.4-0.8. To induce the His-fused OmpA fragment protein expression, the iso-propyl-β-D-thiogalactopyranoside (IPTG) was added to a final concentration of 0.5 mM in the culture, and further incubated for 4 to 6 hr at 37° C. After incubation, the cells were collected. The pellet were re-suspended in Histidine (His) binding buffer and disrupted by sonication. After centrifugation, the total proteins containing His-fused protein were mixed with 50% Ni Sepharose High Performance solution (Amersham Biosciences, Sweden) and incubated at room temperature for 0.5 to 1 hr. The mixtures were centrifuged at 500 g for 5 min and the bead pellets were washed with 5 volumes of His washing buffer for 5 min. The wash steps were repeated at least twice to increase the purity of His-fused proteins. Finally, the His elution buffer was added and incubated for 15-20 min. The supernatants were collected after centrifugation at 500 g for 5 min.

Immunization of Chickens with Purified His-Fused OmpA Proteins

Adult female white Leghorn chickens were immunized with the antigen mixture four times at 7-day intervals. The first immunizing antigens were prepared by mixing 50 µg purified His-fused proteins in 500 µl Phosphate-buffer saline (PBS) with equal volume of complete Freund's adjuvant. For subsequent immunization, antigens were mixed with incomplete Freund's adjuvant instead. Eggs laid by chickens before and after immunization were collected daily and stored at 4° C.

Purification of Total IgY Antibodies in Chicken Eggs

Egg yolk was separated from the egg white and diluted with 4 volumes of TBS. After centrifugation at 2000-3000 g for 20 min at 25° C., 120 µl of dextran sulphate solution was added per ml of the supernatant, mixed well and incubated for 30 min at 25° C., followed by adding 50 µl calcium chloride per ml of the supernatant and proceeding as above. The mixture was centrifuged at 2000-3000 g for 20 min at 25° C. and the volume of the supernatant was adjusted to 100 ml with TBS. The solution was stirred while slowly adding 20 g of anhydrous sodium sulfate until completely dissolved and then let to stand for 30 min at 25° C. After centrifugation as above, the precipitate was re-dissolved in 10 ml TBS, which was centrifuged again to collect the supernatant. The precipitation of total IgY antibodies was repeated again by slowly adding 8 ml of 36% sodium sulfate solution. The final pellet was re-dissolved in 5 ml TBS containing a 0.05% sodium azide and stored at 4° C.

Western Blotting

Figure 8:
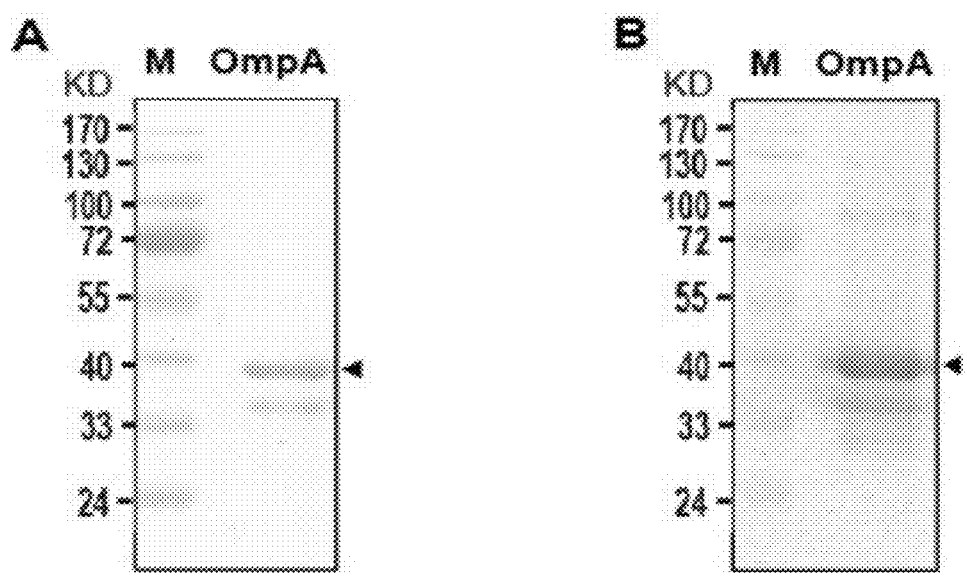
FIG. 8 shows the analysis of purified OmpA proteins using SDS-PAGE and Western blotting. Plot A is SDS-PAGE; plot B is Western blotting; M is a marker; and the protein at around 40 kDa is OmpA.
Figure 9:
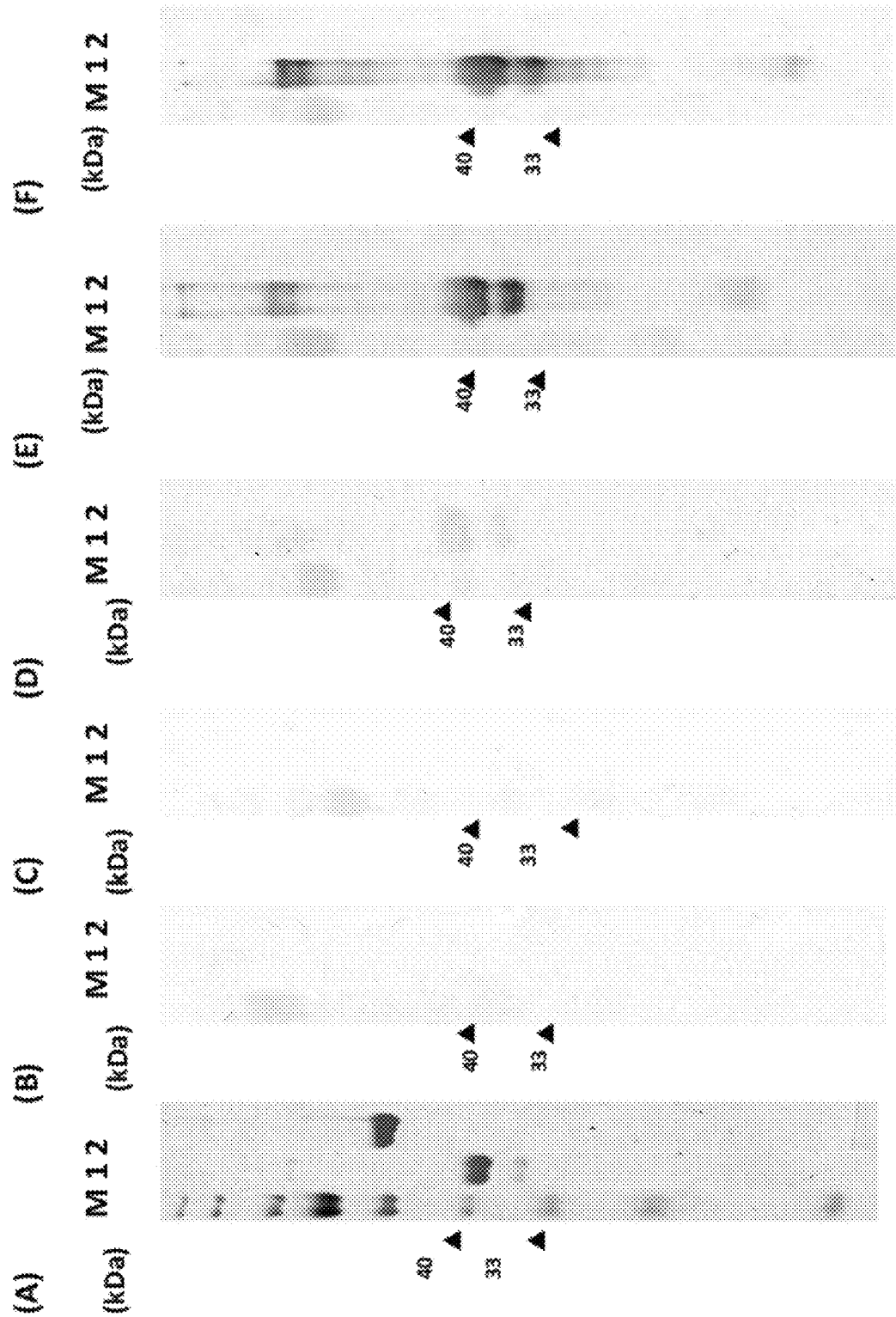
FIG. 9 shows the binding of polyclonal anti-OmpA IgY antibodies to OmpA on Western blots. Panel (A): Coomassie blue stained SDS-PAGE. Panels (B) to (F): Western blots incubated with IgY antibodies purified from eggs laid by chickens with pre-, first, second, third and fourth immunizations and then HRP-conjugated donkey anti-chicken IgY (1:10000) for detecting humoral responses in chickens. Lanes 1 and 2 in each panel are OmpA protein and BSA.

The purified IgY antibodies, different His-fused OmpA proteins and total cellular lysates from wild-type and mutant E. coli strains were loaded on a SDS-PAGE and transferred to the nitrocellulose membrane. The nitrocellulose membrane containing proteins was blocked with 5% skim milk. Mouse anti-His antibody (Amersham Biosciences, UK) by 1:5,000 dilution and produced anti-OmpA IgY antibodies (1:10,000) were added as the primary antibody respectively for 1 hr at room temperature. The membranes were washed three times with PBST (PBS with 0.05% Tween-20) and incubated with HRP-conjugated donkey anti-chicken IgY Ab by 1:10,000 dilution (Jackson ImmunoResearch, USA) anti-His antibodies for 1 hr at room temperature. After washing three times, the protein bands were developed with DAB until reaching desired intensity. In FIG. 8 (A) SDS-PAGE shows the purified OmpA and (B) is a Western blot showing that the anti-OmpA IgY antibodies specifically bind to OmpA. In FIG. 9. (A) SDS-PAGE shows the purified OmpA and (B) to (F) are Western blots showing the binding of the OmpA to IgY antibodies purified from eggs laid by chickens with pre-, first, second, third and fourth immunizations wherein HRP-conjugated donkey anti-chicken IgY is used as the secondary antibody in Western blotting.

Enzyme-Link Immunosorbent Assay (ELISA)

His-fused OmpA proteins and BSA were coated with 0.5 µg/well of in 96-well ELISA plate (Becton Dickinson and company, USA) for 1 hr at 37° C. The wells were blocked by 5% skim milk for 1 hr at 37° C. Polyclonal IgY antibodies from pre- and 4$^{th}$ immunized chickens were diluted and incubated with the coated antigens for 1 hr at 37° C. BSA was used as a negative control. After incubation, the wells were washed with PBST at least 3 times. HRP-conjugated donkey anti-chicken IgY antibodies was used as the secondary antibody at 1:10,000 dilution and incubated for another hour at 37° C.

Figure 10:
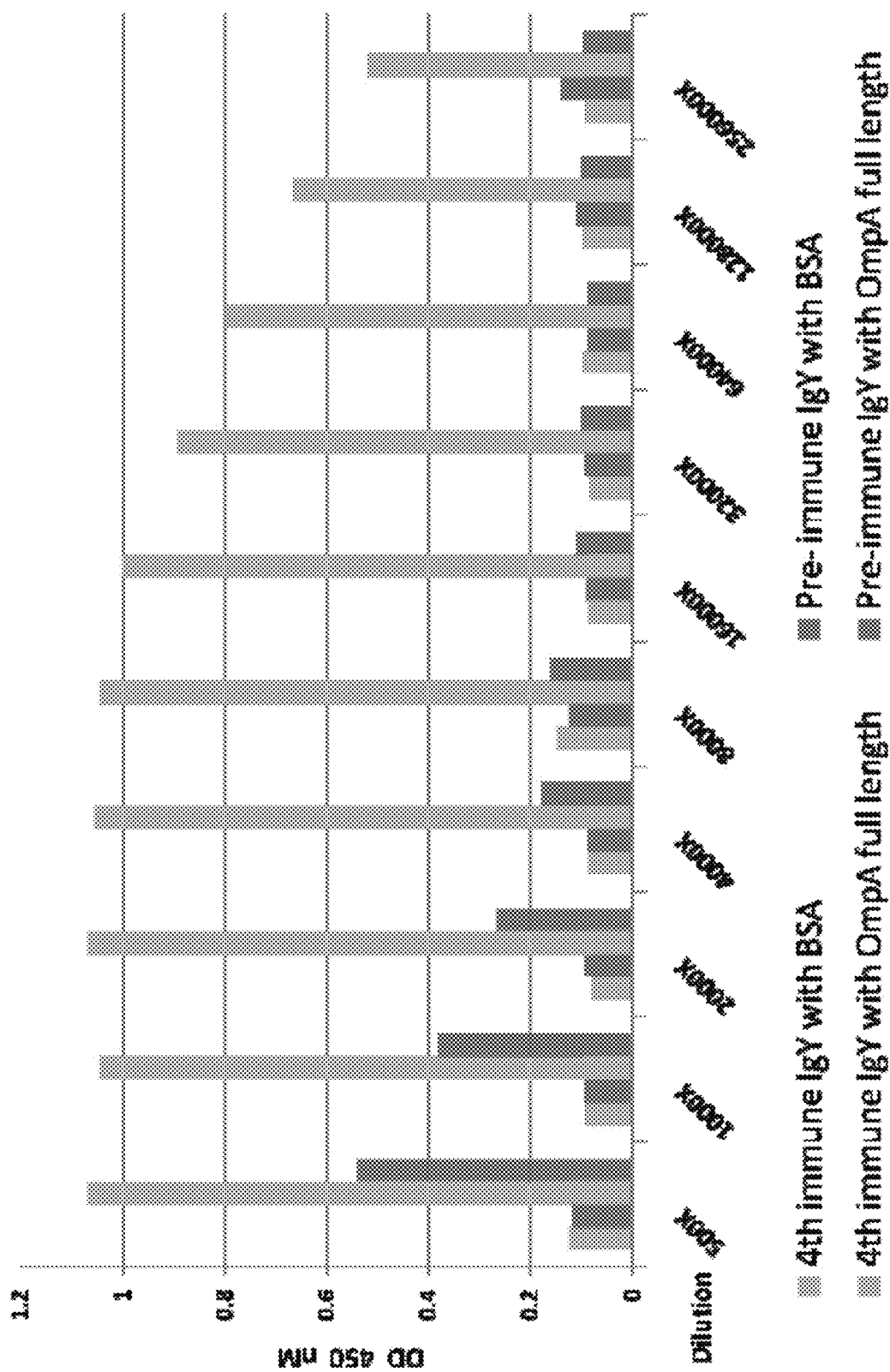
FIG. 10 shows the binding of polyclonal anti OmpA IgY antibodies to OmpA on ELISA.

After washing as above, the binding was visualized by adding 25 μl of TMB into each well. Finally, 25 μl of 1N HCL was added to stop the color development and optical density (OD) at 450 nm was measured by an ELISA plate reader. FIG. 10 shows the specific binding of the polyclonal anti-OmpA IgY antibodies in different dilutions to His-fused OmpA on ELISA. The IgY with BSA was used as a non-specific control. The results indicate that the 8,000× to 16,000× dilutions of the polyclonal anti-OmpA IgY antibodies are most appropriate concentrations for binding.

Immunocytochemistry

Figure 11:
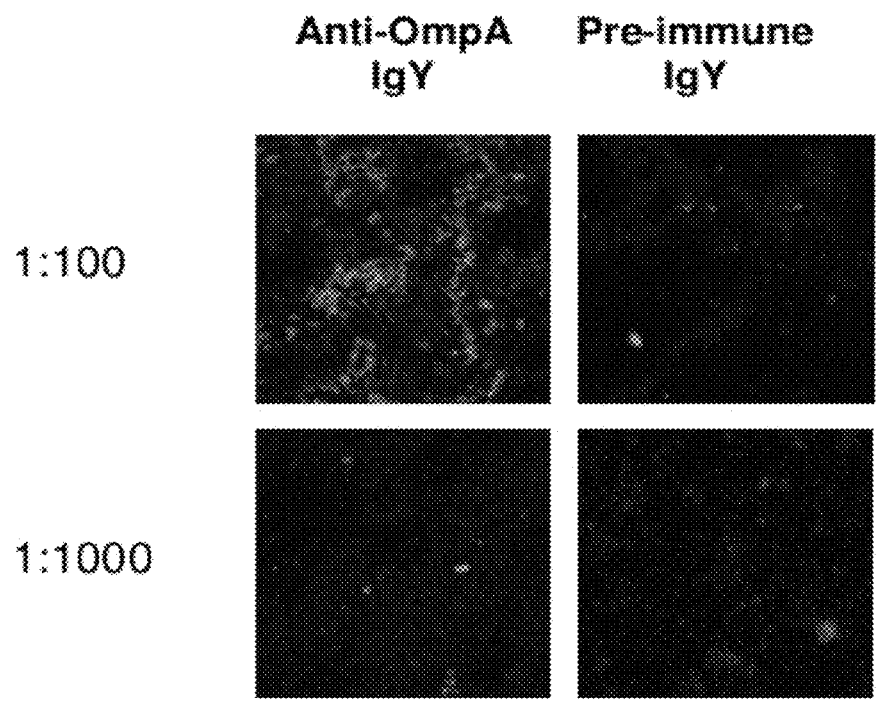
FIG. 11 shows the binding of anti-OmpA IgY antibodies to *E. coli* E44 using Confocal Spectral Microscope Imaging System.

C6 glioma cell monolayers were infected with *E. coli* and fixed with 4% paraformaldehyde. The resulting C6 cell samples were blocked with 1% BSA and then incubated with a solution containing polyclonal chicken anti-OmpA IgY Ab (diluted 1:100 and 1:1000) from chicken so that the anti-OmpA IgY Ab could bind to the OmpA of *E. coli*. Polyclonal IgY Ab from non-immunized chicken was used as a negative control. Finally, samples were incubated with FITC-labeled anti-IgY secondary antibody (diluted 1:500). Slides were mounted in 50% glycerol-PBS, and then examined with TCS SP5 Confocal Spectral Microscope Imaging System (Leica). FIG. 11 shows that the anti-OmpA antibodies produced clearly bind to E44, whereas IgY from non-immunized chicken did not show any binding activity.

Example 4

Figure 12:
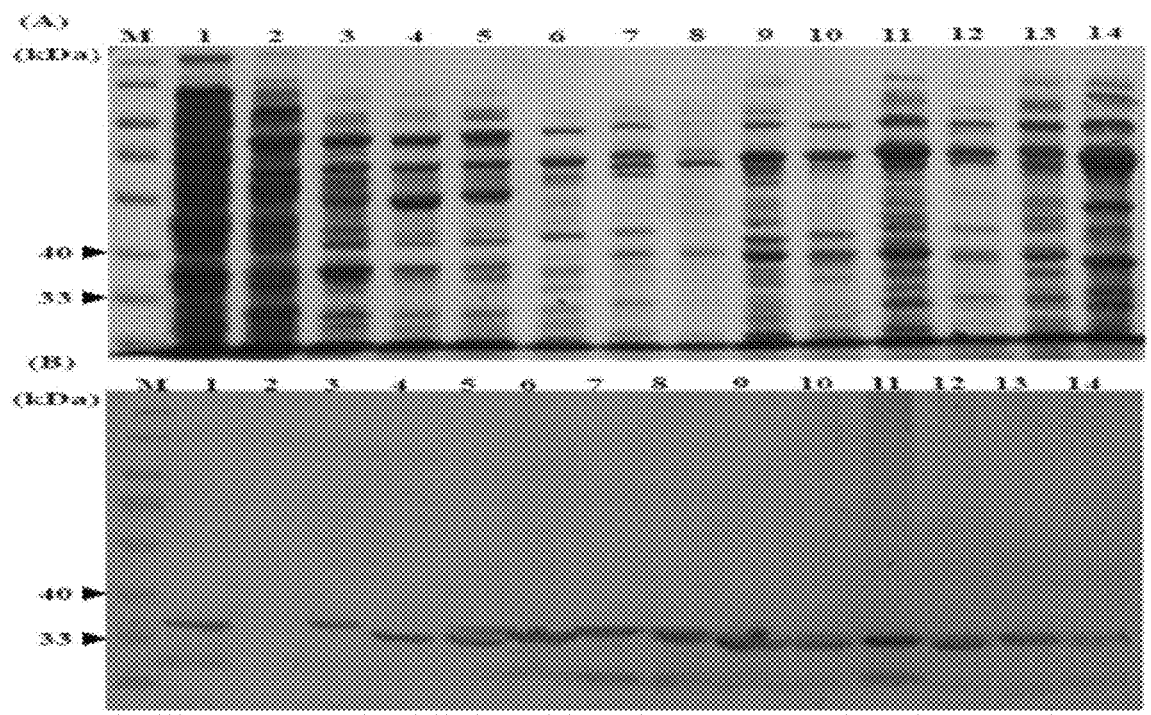
FIG. 12 shows SDS-PAGE gels of Enterobacteriaceae bacteria strain OmpA protein (FIG. 12 (A)) and the detection of Enterobacteriaceae bacteria strain OmpA protein by Western blotting (FIG. 12 (B)). Lanes 1 to 14 are OmpA proteins from *E. coli* E44, E91, clinic *E. coli* isolate, *S. sonnei*, *S. flexneri*, *Salmonella* group A, *Salmonella* group B, *Salmonella* group D, *C. freundii*, *C. koseri*, *K. oxytoca*, *E. aerogenes*, *E. cloacae* and *S. marcescens*. were detected using polyclonal anti-OmpA antibodies produced in chickens.

Detection of Enterobacteriaceae Bacteria Strain OmpA Protein by Western Blotting Bacterial solutions of *E. coli* E44, E91, clinic *E. coli* isolate, *S. sonnei, S. flexneri, Salmonella* group A, *Salmonella* group B, *Salmonella* group D, *C. freundii, C. koseri, K. oxytoca, E. aerogenes, E. cloacae* and *S. marcescens* were centrifuged at 3,500 rpm for 10 min and the supernatants were discarded to collect bacterial proteins. The resulting bacterial proteins were appropriately diluted and denatured by adding a protein loading dye containing beta-mercaptoethanol. The denatured proteins were isolated by SDS-PAGE electrophoresis. Coomassie blue stain was performed on one of the resulting SDS-PAGE gels. West blotting as mentioned in Example 4 was performed on the other gel. FIG. 12 shows that *E. coli, S. sonnei, S. flexneri, Salmonella* group A, *Salmonella* group B, *Salmonella* group D, *C. freundii, C. koseri, K. oxytoca, E. aerogenes, E. cloacae* and *S. marcescens* can be detected by the anti-OmpA IgY antibodies of Example 4 obtained by vaccinating with *E. coli* OmpA. *E. coli* (Genus: *Escherichia*), *S. Sonnei* (Genus: *Shigella*) and *S. flexneri* (Genus: *Shigella*) are representative species of Eschichieae; *Salmonella* group A (Genus: *Salmonella*), *Salmonella* group B (Genus: *Salmonella*) and *Salmonella* group D (Genus: *Salmonella*) are representative species of Salmonelleae; *C. freundii* (Genus: *Citrobacter*) and *C. koseri* (Genus: *Citrobacter*) are representative species of Citrobactereae; and *K. pneumoniae* (Genus: *Klebsiella*) (see the results of Example 2), *K. oxytoca* (Genus: *Klebsiella*), *E. aerogenes*, (Genus: *Enterobacter*), *E. cloacae* (Genus: *Enterobacter*) and *S. marcescens* (Genus: *Serratia*) are representative strains of Klebsielleae, so the detection of the above-mentioned bacteria supports that the infection of Enterobacteriaceae bacteria can be detected by the anti-OmpA antibodies and treated by the administration of OmpA because Eschichieae, *Salmonellea, Citrobactereae* and *Klebsielleae* are representative families of Enterobacteriaceae bacteria.

Example 5

Invasion Assay of Chicken OmpA IgY Antibodies of the Invention

The glioma C6 confluent cell monolayers were incubated with the above-mentioned bacteria strain (MOI=10) at indicated time intervals at 37° C. The monolayers were then washed with culture medium three times and further incubated with culture medium containing gentamicin (100 μg ml$^{-1}$) for 2 hours to kill extracellular bacteria. The monolayers were washed three times again and lysed in 0.5% Triton X-100. The released bacteria were enumerated by plating on sheep blood agar plates. In the invasion inhibition assay, the glioma C6 confluent cell monolayers were infected with *E. coli* E44 (MOI=10) with 4 μg or 40 μg OmpA for 2 hours. The monolayers were then washed with culture medium three times and further incubated with culture medium containing gentamicin (100 μg ml$^{-1}$) for 2 hours to kill extracellular bacteria. The released bacteria were enumerated by plating on sheep blood agar plates. As shown in FIG. 3, the mixtures of *E. coli* E44 and OmpA indeed inhibit the invasion of *E. coli* E44. OmpA can inhibit more than 55% (4 μg) and 80% (40 μg) invasion of *E. coli* E44.

Figure 13:
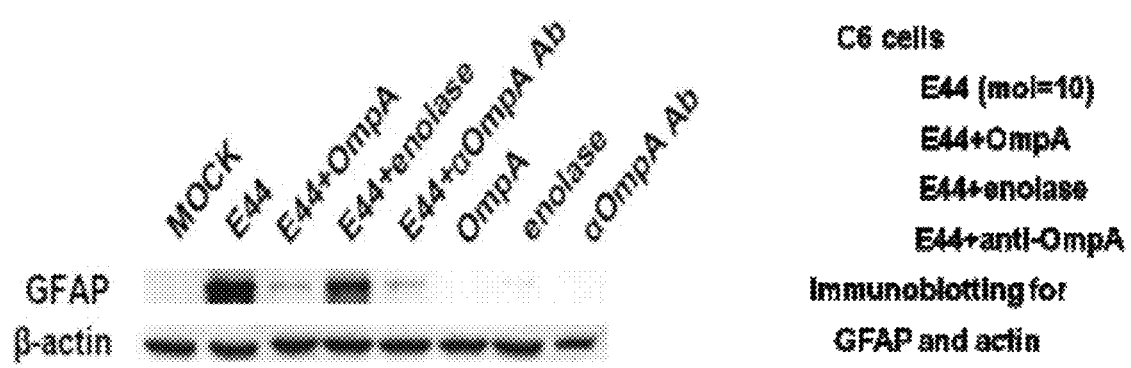
FIG. 13 shows that OmpA IgY antibodies can specifically inhibit *E. coli* E 44 invasion and activation of C6 cells.

The invasion assay of chicken OmpA IgY antibodies were performed according to the materials and procedures mentioned in Example 1. A blank was used in the assay wherein C6 cells without any agent (see MOCK in FIG. 13). Two positive controls were used in the assay wherein (1) C6 cells were infected with *E. coli* E44 (see E44 in FIG. 13); and (2) C6 cells were infected with *E. coli* E44 and then OmpA was added to the cells (see E44+OmpA in FIG. 13). Four negative controls were used in the assay wherein (1) C6 cells were infected with *E. coli* E44 and then enolase was added to the cells (see E44+enolase); (2) OmpA was added to C6 cells (see OmpA in FIG. 13); (3) enolase was added to C6 cells (see enolase); and (4) anti-OmpA IgY antibodies were added to C6 cells (see α OmpA Ab). The experimental group used in the assay is that C6 cells were infected with *E. coli* E44 and anti-OmpA IgY antibodies were added to the cells (see E44+α OmpA Ab). Subsequently, immunoblotting was conducted wherein β-actin is used as control. GFAP is a protein that exits in brain cells such as C6 cells. When C6 cells are infected with *E. coli*, their expression increase. FIG. 13 shows that OmpA IgY antibodies can specifically inhibit *E. coli* E44 invasion. Particularly, the expression level of GFAP significantly reduced in E44+αOmpA Ab group.

What is claimed is:

1. A method for the treatment of bacterial infection caused by *Escherichia coli, Shigella sonnei, Shigella flexneri, Salmonella typhi, Salmonella* group A, *Salmonella* group B, *Salmonella* group D, *Citrobacter freundii, Citrobacter koseri, Klebsiella pneumoniae, Klebsiella oxytoca, Enterobacter aerogenes, Enterobacter cloacae* or *Serratia marcescens* in central nervous system and/or peripheral blood circulation in a mammal, which comprises administering to said mammal an effective amount of an outer membrane protein A (OmpA) from *Escherichia coli, Shigella sonnei, Shigella flexneri, Salmonella typhi, Salmonella* group A, *Salmonella* group B, *Salmonella* group D, *Citrobacter freundii, Citrobacter koseri, Klebsiella pneumoniae, Klebsiella oxytoca, Enterobacter aerogenes, Enterobacter cloacae* or *Serratia marcescens*.

2. The method of claim 1, wherein the mammal is human.

3. The method of claim 1, wherein the OmpA is a recombinant OmpA.

4. The method according to claim 1, wherein the OmpA is obtained from *Escherichia coli, Klebsiella pneumoniae, Salmonella typhi*, or *Enterobacter aerogenes*.

5. The method according to claim 1, wherein the bacterial infection is caused by *Escherichia coli, Klebsiella pneumoniae, Salmonella typhi*, or *Enterobacter aerogenes*.

6. The method according to claim 1, wherein the OmpA is administrated orally or via intravenous injection.

7. The method according to claim 1, wherein the OmpA is administrated at an amount of 0.0001% to 10% by weight of OmpA.

8. The method according to claim 1, wherein the OmpA is administrated at an amount of 0.5% to 5% by weight of OmpA.

9. A method for vaccinating a mammal to produce an antibody against bacterial infection caused by *Escherichia coli, Shigella sonnei, Shigella flexneri, Salmonella typhi, Salmonella* group A, *Salmonella* group B, *Salmonella* group D, *Citrobacter freundii, Citrobacter koseri, Klebsiella pneumoniae, Klebsiella oxytoca, Enterobacter aerogenes, Enterobacter cloacae* or *Serratia marcescens* in central nervous system and/or peripheral blood circulation, which comprises administering to said mammal an effective amount of an OmpA from *Escherichia coli, Shigella sonnei, Shigella flexneri, Salmonella typhi, Salmonella* group A, *Salmonella* group B, *Salmonella* group D, *Citrobacter freundii, Citrobacter koseri, Klebsiella pneumoniae, Klebsiella oxytoca, Enterobacter aerogenes, Enterobacter cloacae* or *Serratia marcescens*.

10. The method of claim 9, wherein the antibody is a polyclonal antibody.

11. The method of claim 9, wherein the mammal is human.

12. The method of claim 9, wherein the OmpA is a recombinant OmpA.

13. The method of claim 9, wherein the OmpA is obtained from *Escherichia coli, Klebsiella pneumoniae, Salmonella typhi*, or *Enterobacter aerogenes*.

14. The method according to claim 9, wherein the OmpA is administrated at an amount of 0.0001% to 10% by weight of OmpA.

15. The method according to claim 9, wherein the OmpA is administrated at an amount of 0.5% to 5% by weight of OmpA.

* * * * *